United States Patent [19]

Hansson et al.

[11] Patent Number: 5,588,838
[45] Date of Patent: Dec. 31, 1996

[54] FIXTURE FOR USE IN A DENTAL IMPLANT SYSTEM

[75] Inventors: Stig G. V. Hansson, Askim; Anders Holmén, Sweden, both of Sweden

[73] Assignee: Astra Aktiebolag, Södertälje, Sweden

[21] Appl. No.: 424,404

[22] PCT Filed: Oct. 25, 1993

[86] PCT No.: PCT/SE93/00871

§ 371 Date: Apr. 26, 1995

§ 102(e) Date: Apr. 26, 1995

[87] PCT Pub. No.: WO94/09717

PCT Pub. Date: May 11, 1994

[30] Foreign Application Priority Data

Oct. 28, 1992 [SE] Sweden ..................... 9203184

[51] Int. Cl.⁶ ........................................ A61C 8/00
[52] U.S. Cl. ........................... 433/173; 433/174
[58] Field of Search ........................ 433/172, 173, 433/174, 175, 176

[56] References Cited

U.S. PATENT DOCUMENTS

| | | | |
|---|---|---|---|
| 4,468,200 | 8/1984 | Munch | 433/174 |
| 4,723,913 | 2/1988 | Bergman | 433/173 |
| 4,826,434 | 5/1989 | Kruger | 433/174 |
| 4,988,299 | 1/1991 | Branemark | 433/174 |
| 5,004,421 | 4/1991 | Lazarof | 433/174 X |
| 5,007,835 | 4/1991 | Valen | 433/174 |
| 5,061,181 | 10/1991 | Niznick | 433/174 |
| 5,310,343 | 5/1994 | Hasegawa et al. | 433/173 |
| 5,344,457 | 9/1994 | Pilliar et al. | 433/174 X |
| 5,366,374 | 11/1994 | Vlassis | 433/173 X |
| 5,484,286 | 1/1996 | Hannson . | |

FOREIGN PATENT DOCUMENTS 0388576 11/1989 European Pat. Off. .

Primary Examiner—Nicholas D. Lucchesi
Attorney, Agent, or Firm—White & Case

[57] ABSTRACT

A fixture, for use in a dental implant system, of the type having an upper portion with a conically flaring outer surface. The conically flaring outer surface is provided with a circumferentially oriented, defined micro-roughness, preferably in the form of threads or beads, having a height between 0.02 and 0.20 mm, and most preferably approximately 0.1 mm. In the preferred embodiment, the distance between adjacent threads or beads, crest to crest, is approximately twice the height of the threads or beads, respectively.

9 Claims, 1 Drawing Sheet

FIXTURE FOR USE IN A DENTAL IMPLANT SYSTEM

The present invention relates to fixtures for dental implants, i.e. the parts of dental implant systems which are to be implanted in the bone tissue, and particularly to fixtures whose outer end or neck are provided with a conically flaring portion intended to at least partly abut the bone tissue.

BACKGROUND TO THE INVENTION

Fixtures having a cylindrical main body and a conically flaring upper portion or neck have been known and used in the art of dental implants for a long period of time. These fixtures are to be inserted into bore-holes in the jaw-bone in order to become osseointegrated to the bone tissue. The cylindrical parts generally osseointegrate correctly provided the proper techniques are used.

There are however some difficulties regarding the osseointegration around the conical neck portion of the implants which portion normally is smooth or polished. For some reason the bone tissue may degenerate around a smooth or polished conical part (bone resorbtion), leaving a pocket in the bone tissue around the conical part. The mechanism behind this is not quite clear. These pockets normally are accepted as inevitable although it is not entirely satisfactory that the implant is not entirely osseointegrated particularly since this pocket is formed in the strongest part of the bone tissue, the cortical bone.

SHORT DESCRIPTION OF THE INVENTIVE CONCEPT

It surprisingly has been found that the provision of a circumferentially or tangentially oriented, defined micro-roughness on the outer side of the conically flaring portion of the fixture having a height which may vary between 0.02 and 0.20 mm alleviates this problem, the risk for pockets in the bone tissue around the conically flaring portion being minimized.

In preferred embodiments the micro-roughness, as set forth in the appended dependent claims, may be in the form of circumferential beads or microthreads.

SHORT DESCRIPTION OF THE APPENDED DRAWINGS

DETAILED DESCRIPTION OF A PREFERRED EMBODIMENT OF THE INVENTION

Figure 1:
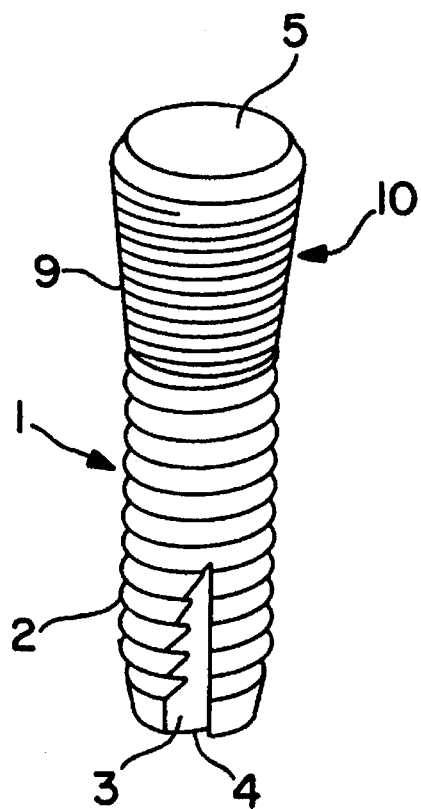
FIG. 1 shows the exterior of a fixture according to the invention.

In the description below, the invention is illustrated by means of micro-threads. It should be noted that the description in the relevant parts (i.e. the parts not relating directly to the helical nature of the threads) also is applicable to the embodiment featuring the circumferential beads and that this choice does not reflect any preference regarding the two embodiments.

Thus, in a preferred embodiment, the invention comprises an implant or fixture having a generally cylindrical body 1 for insertion into a bore-hole into bone tissue. The envelope surface of the body 1 is provided with conventional threads 2. These threads will allow the implant to function as a screw. The forward end or the tip of the screw is provided with three cutting edges 4 together with chip-collecting cavities 3.

The cutting edges 4 and the chip-collecting cavities 3 will allow the screw, if necessary, to function as a self-tapping screw for cutting new threads or adjusting already cut threads in the tissue.

The other end of the screw is, as is quite conventional in the art, provided with a longitudinal bore for the attachment of an abutment for bridging the soft tissue covering the bone tissue and for the attachment of a prosthesis. The inner part 7 of the bore is cylindrical and provided with interior threads 6 and the outer part 5 of the bore, which is located in a portion 10 having a conically flaring outer surface, is conically flaring in order to accommodate a conically tapering attachment part of an abutment. The transitional portion between the conical part and the cylindrical bore comprises a hexagonal socket 8 which is intended to cooperate with a corresponding, hexagonal part of the abutment in order to allow the abutment to be oriented and locked in specific rotational positions relative to the fixture.

Figure 2:
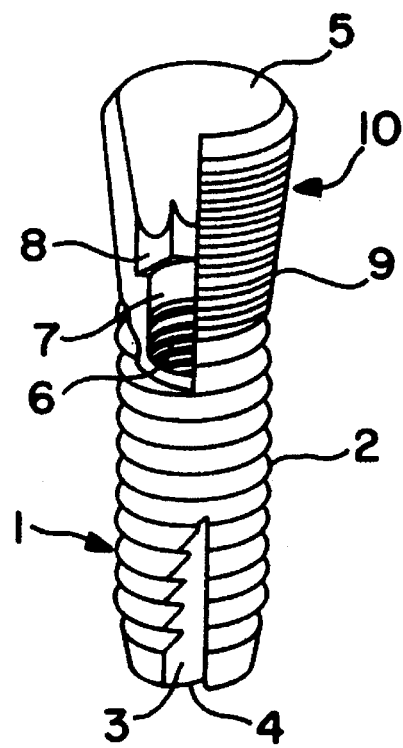
FIG. 2 shows the fixture in FIG. 1, partly sectioned.

As can be seen in FIGS. 1 and 2, the outer surface of the conically flaring portion 10 is provided with threads 9 serving as oriented micro-roughness. The threads 9 may be 0.1 mm high and the distance to the adjacent thread (crest to crest) may be 0.2 mm. The threads 9 are here called microthreads (and the beads microbeads) since their height and distance from each other are in the micrometer range. The microthreads 9 may be multiple-threaded, for instance triple-threaded which means that the pitch of the thread would be 0.6 mm. The angle between the flanks of a microthread may for instance be 45° or 60°. The microthreads 9 have a rounded design in order to avoid, or at least minimize, stress-concentrations in the bone tissue around the microthreads 9.

Generally, the height of the microthreads may be within the range of 0.02–0.20 mm. In a preferred embodiment the height may vary between 0.02 and 0.15 mm, in a more preferred embodiment between 0.05 and 0.15 and in a most preferred embodiment, described above, the height is 0.1 mm. The number of threads is optional but may for instance vary between 1 and 5.

The microthreads can be regarded as a defined, oriented roughness being in the same size range as the kind of prior art non-oriented surface roughness, which for instance may be obtained by plasma-spraying (a conventional technique for obtaining a surface roughness on implants). A non-oriented roughness having smaller dimensions, for instance obtained by blasting, may be superimposed on the microthreads.

New bone tissue will rapidly grow into the microthreads due to the low height of the threads and a retention which is considerably better in the axial direction than in the rotational (tangential) direction will be obtained relatively fast. This of course is a result of the threads being oriented circumferentially.

It would seem that the positive results obtained by this design may be explained as follows:

When the bone tissue has grown into the spaces between individual projections of the micro-roughness, the axial loads on the implant may be transmitted in an axial direction (related to the axial direction of the fixture) to the bone tissue around the conical portion in a biomechanically correct way, i.e. in such a way that the bone tissue is stressed correctly around the conical part and that bone resorbtion consequently does not occur.

Above, the fixture has been described as having normal threads on the cylindrical main body. It may however be particularly advantageous if both the main body and the conically flaring part is provided with microthreads, since this will allow the fixture to be used both as a fixture which gently can be tapped or pushed into the bore-hole and as a fixture which easily can be screwed into, or unscrewed from, the bore-hole.

Figure 3:
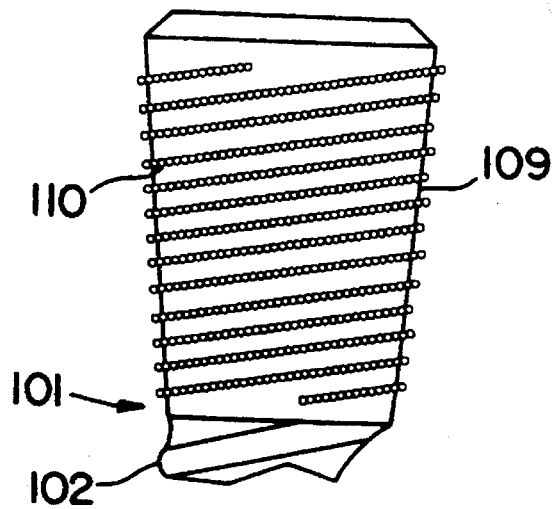
FIG. 3 is a front view of an alternative embodiment of a fixture.

FIG. 3 shows an alternative embodiment of a fixture 101 which includes a cylindrical, threaded body 102, which may be the same as cylindrical portion 1 of FIGS. 1–2, and an upper portion 110 having a conically flaring outer surface. Upper portion 110 may be the same as upper portion 10 of FIGS. 1–2 except that, in place of the microthreads employed in the embodiment of FIGS. 1–2, the conical outer surface of the upper portion 110 of the fixture 101 has circumferentially oriented beads 109. The beads may have a height, spacing, and orientation similar to that of the microthreads 9 described in connection with FIGS. 1–2.

It should be emphasized that the invention is not limited to the embodiments described above and can be varied in many ways within the scope of the appended claims.

We claim:

1. In a fixture for use in a dental implant system, said fixture having an outer end provided with a conically flaring outer surface intended to at least partly abut the bone tissue, the improvement wherein said conically flaring outer surface is provided with a circumferentially oriented, defined micro-roughness (9, 109) having a height between 0.02 and 0.20 mm.

2. A fixture according to claim 1, wherein said micro-roughness has a height between 0.02 and 0.15 mm.

3. A fixture according to claim 2, wherein said micro-roughness has a height between 0.05 and 0.15 mm.

4. A fixture according to claim 2 or 3, wherein said micro-roughness has a height of 0.1 mm.

5. A fixture according to claim 2 or 3, wherein said micro-roughness comprises circumferentially oriented projections, each having a crest, and wherein the distance between projections, crest to crest, is approximately twice the height of the projections.

6. A fixture according to claim 4, wherein said micro-roughness comprises circumferentially oriented projections, having a crest, and wherein the distance between projections, crest to crest, is approximately twice the height of the projections.

7. A fixture according to claim 1, wherein the defined micro-roughness is in the form of circumferential beads (109).

8. A fixture according to claim 1, wherein the defined micro-roughness is in the form of a microthread (9).

9. A fixture according to claim 7 or 8, wherein the distance between adjacent threads or beads, crest to crest, is approximately twice the height of the threads or beads, respectively.

* * * * *